United States Patent [19]  [11] Patent Number: 4,556,729
Kubo et al.  [45] Date of Patent: Dec. 3, 1985

[54] DIACRYLATE AND METHOD FOR MANUFACTURING THE SAME

[75] Inventors: Motonobu Kubo; Kazumi Honda, both of Iwakuni, Japan

[73] Assignee: Sanyo-Kokusaku Pulp Co., Ltd., Tokyo, Japan

[21] Appl. No.: 628,865

[22] Filed: Jul. 9, 1984

[30] Foreign Application Priority Data

Dec. 7, 1983 [JP] Japan .................................. 58-232112

[51] Int. Cl.$^4$ .............................................. C07C 69/54
[52] U.S. Cl. ...................................... 560/220; 526/309
[58] Field of Search ............................................. 560/220

[56] References Cited

U.S. PATENT DOCUMENTS 3,730,947 5/1973 Stoffey et al. ........................ 560/220
3,770,602 11/1973 D'Alelio .......................... 204/159.15

OTHER PUBLICATIONS

Clark, N. G., *Modern Organic Chemistry* (1964) Oxford University Press, at p. 205.

*Primary Examiner*—Natalie Trousof
*Assistant Examiner*—L. Hendriksen
*Attorney, Agent, or Firm*—Armstrong, Nikaido, Marmelstein & Kubovcik

[57] ABSTRACT

A novel diacrylate or dimethacrylate characterized in that diols having two allyloxy groups in a molecule are esterified with acrylic acid, methacrylic acid or their derivatives, and represented by the following structural formula:

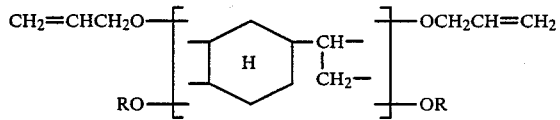

wherein R denotes acryloyl or methacryloyl group, and a method for manufacturing the same.

3 Claims, 1 Drawing Figure

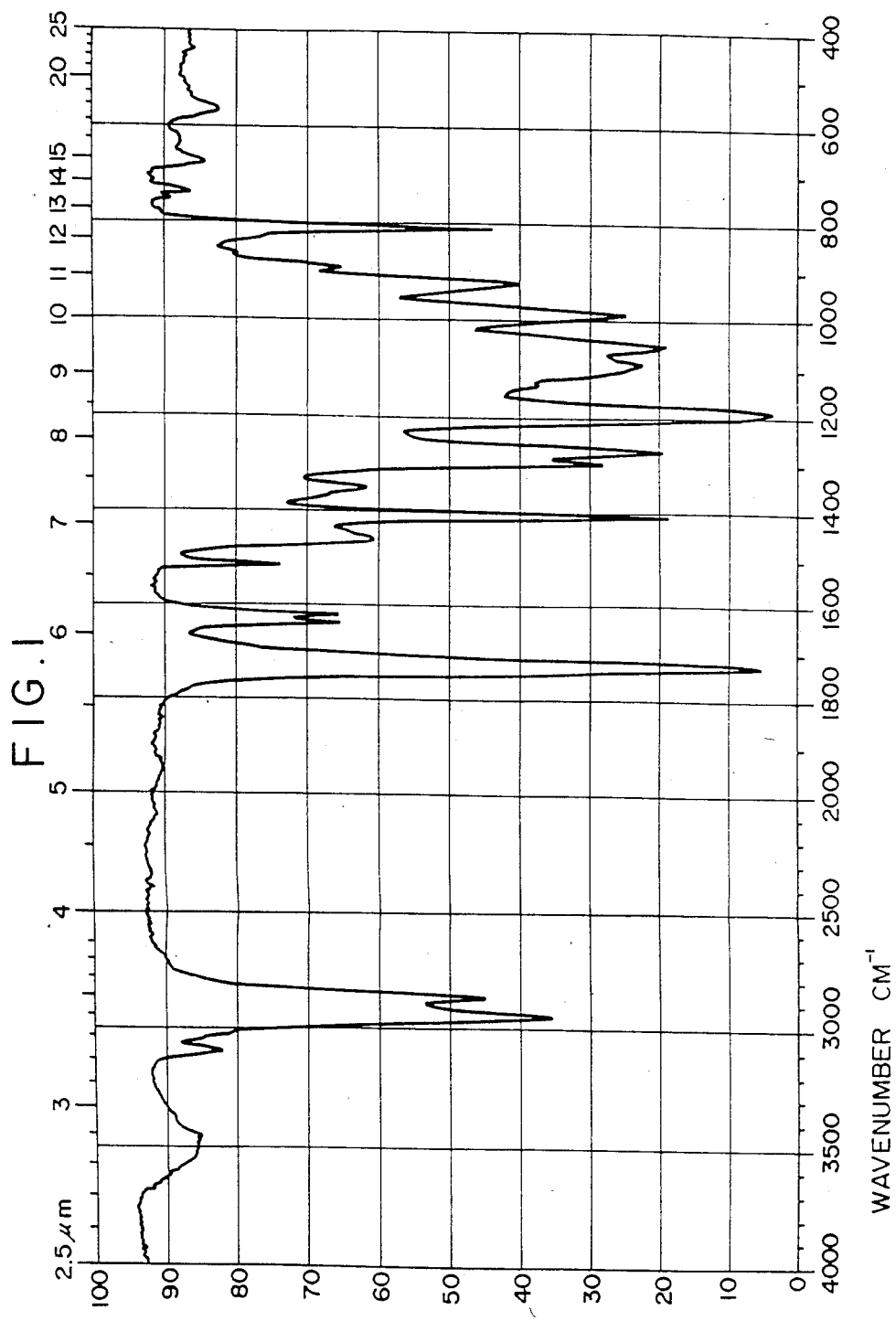

DIACRYLATE AND METHOD FOR MANUFACTURING THE SAME

DETAILED DESCRIPTION OF THE INVENTION

The present invention relates to di(meth)acrylate represented by the structural formula (I), that is, 1(or 2)-allyloxy-2(or 1)-(meth)acryloyloxy-4[1(or 2)-allyloxy-2(or 1)-((meth)acryloyloxy)ethyl]cyclohexane.

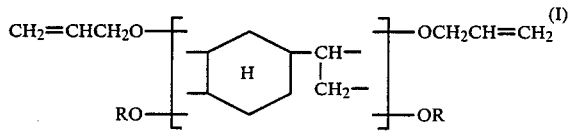

wherein R denotes acryloyl or methacryloyl group, and a method for manufacturing the same.

This compound is a novel substance and has two each of allyl group and (meth)acryl group in a molecule. Therefore, it is useful as a crosslinking modifier or a curing accelerator on the copolymerization with other vinyl monomers and also as a crosslinking curing accelerator of unsaturated polyester.

The compound shown in the structural formula (I) [hereinafter referred to as compound (I)] can be obtained by esterifying a compound shown in the following structural formula (II) [hereinafter referred to as compound (II)], that is, 1(or 2)-allyloxy-2(or 1)-hydroxy-4[1(or 2)-allyloxy-2(or 1)-(hydroxy)ethyl]cyclohexane with (meth)acrylic acid or its derivatives. Thereby, the compound (II) is obtained through the ring-opening of oxirane rings of 4-vinylcyclohexane dioxide in the presence of allyl alcohol.

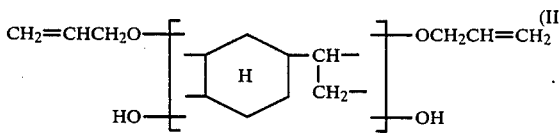

When esterification is carried out using (meth)acrylic acid, either sulfuric acid or p-toluenesulfonic acid may be used as a catalyst. Also, as a polymerization inhibitor used in the reaction process, such one as being removed easily by washing with aqueous alkaline solution, exemplified by hydroquinone, hydroquinone monomethyl ether, cuprous chloride, etc., is preferable.

As an azeotropic solvent used for the purpose of bringing off the water formed through the esterification reaction outwards the system, single or mixed organic solvent capable of forming an azeotropic mixture with water and substantially immiscible with water each other, exemplified by benzene, toluene, xylene, n-hexane, methyl isobutyl ketone, etc., can be used.

It is also possible to manufacture compound (I) through the transesterification reaction of compound (II) with (meth)acrylic ester. In this case, the transesterification reaction is carried out by means that the publicly known (meth)acrylic ester such as methyl-, ethyl-, butyl-, n-propyl- or isopropyl-ester of (meth)acrylic acid is heated with compound (II) in the presence of the polymerization inhibitor and the catalyst, and said lower alcohol formed is brought off outwards the system.

As the polymerization inhibitor used in this case, hydroquinone, hydroquinone monomethyl ether or the like is used when using sulfuric acid or p-toluenesulfonic acid as a catalyst in the transesterification reaction, and alkaline polymerization inhibitor, for example, p-phenylenediamine or phenyl-$\beta$-naphthylamine is used when using alkaline catalyst such as metallic sodium, sodium alcoholate or the like.

BRIEF DESCRIPTION OF THE DRAWING

FIG. 1 is one showing infrared absorption spectrum of compound obtained in Example 1.

EXAMPLE 1

Into a reaction vessel equipped with the reflux condenser, water separator and agitator, 256 g of compound (II), 180 g of acrylic acid, 10 g of p-toluenesulfonic acid and 20 g of hydroquinone monomethyl ether were put together with 400 ml of toluene and heated for 16 hours under agitation. After separated the water from toluene-water distillate in the water separator, toluene was returned continuously to the reaction vessel. Water obtained during this period amounted to 36 g. After the reaction was completed, the product was cooled to room temperature, washed twice with 500 ml of saturated aqueous solution of sodium carbonate, and then washing was repeated with saturated solution of salt until the alkalinity disappeared. To this, 1 g of hydroquinone monomethyl ether was added and toluene was distilled off below 80° C. under vacuum to obtain 341 g of compound (I) in which R is acryloyl group, that is, 1(or 2)-allyloxy-2(or 1)-acryloyloxy-4[1(or 2)-allyloxy-2(or 1)-(acryloyloxy)ethyl]cyclohexane.

In FIG. 1, infrared absorption spectrum of this substance is shown.

Values obtained by elementary analysis (as $C_{20}H_{28}O_6$): Theoretical: C, 65.92%; H, 7.75%. Found: C, 65.41%; H, 7.93%.

EXAMPLE 2

By the similar procedure as described in Example 1 except that 206 g of methacrylic acid were used in place of acrylic acid in Example 1 and the heating time was changed to 20 hours, 362 g of compound (I) in which R is methacryloyl group, that is, 1(or 2)-allyloxy-2(or 1)-methacryloyloxy-4[1(or 2)-allyloxy-2(or 1)-(methacryloyloxy)ethyl]cyclohexane was obtained.

Values obtained by elementary analysis (as $C_{22}H_{32}O_6$): Theoretical: C, 67.32%; H, 8.22%. Found: C, 67.10%; H, 8.30%.

EXAMPLE 3

Into a reaction vessel equipped with Vigrue-type fractionating column and, in addition, a capillary tube so that nitrogen gas can be blown into the bottom of the vessel, 256 g of compound (II), 861 g of methyl acrylate, 25 g of hydroquinone monomethyl ether and 10 g of p-toluenesulfonic acid were placed. These were heated to boiling in the oil bath and maintained under reflux. Methanol formed was distilled off as an azeotropic mixture with methyl acrylate.

After the reaction was continued for 10 hours, excess methyl acrylate was distilled off and the product was cooled to room temperature. This was washed twice with 500 ml of saturated aqueous solution of sodium carbonated, then washed with saturated solution of salt until the alkalinity disappeared, and dried over anhydrous sodium sulfate. As this, 319 g of compound (I) in which R is acryloyl group, that is, 1(or 2)-allyloxy-2(or 1)-acryloyloxy-4[1(or 2)-allyloxy-2(or 1)-(acryloyloxy)ethyl]cyclohexane was obtained.

Values obtained by elementary analysis (as $C_{20}H_{28}O_6$): Theoretical: C, 65.92%; H, 7.75%. Found: C, 65.79%; H, 7.80%.

What is claimed is:

1. A diacrylate derivative represented by the formula (I)

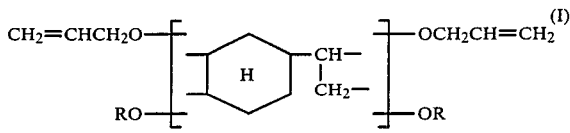

wherein R denotes acryloyl or methacryloyl group.

2. 1(or 2)-allyloxy-2(or 1)-acryloyloxy-4[1(or 2)-allyloxy-2(or 1)-(acryloyloxy)ethyl]cyclohexane represented in claim 1.

3. 1(or 2)-allyloxy-2(or 1)-methacryloyloxy-4[1(or 2)-allyloxy-2(or 1)-(methacryloyloxy)ethyl]cyclohexane.

* * * * *